United States Patent
Gassmann et al.

(10) Patent No.: US 6,447,806 B1
(45) Date of Patent: Sep. 10, 2002

(54) PHARMACEUTICAL COMPOSITIONS COMPRISED OF STABILIZED PEPTIDE PARTICLES

(75) Inventors: Peter Gassmann, Weil (DE); Heinz Sucker, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/668,889

(22) Filed: Sep. 25, 2000

Related U.S. Application Data (63) Continuation of application No. 09/257,126, filed on Feb. 25, 1999, which is a continuation of application No. 08/137,088, filed as application No. PCT/EP92/00862 on Apr. 16, 1992.

(51) Int. Cl.⁷ .............................. A61K 9/14; A61K 9/20; A61K 9/48
(52) U.S. Cl. .................. 424/490; 424/433; 424/436; 424/464; 424/451; 424/455; 424/489; 514/937; 514/944; 514/951; 514/952; 514/969; 514/970
(58) Field of Search ................. 424/490, 498, 424/464, 436, 451, 489, 455, 433

(56) References Cited

U.S. PATENT DOCUMENTS

| | | |
|---|---|---|
| 4,145,410 A | 3/1979 | Sears |
| 4,271,196 A | 6/1981 | Schmidt |
| RE31,609 E | 6/1984 | Sears |
| 4,486,417 A | 12/1984 | Sugimoto et al. |
| 4,826,689 A | 5/1989 | Violanto et al. ............ 424/489 |
| 4,839,111 A | 6/1989 | Huang |
| 4,876,086 A | 10/1989 | Dowrick .................. 424/480 |
| 4,902,500 A | 2/1990 | Jansen et al. |
| 4,960,814 A | 10/1990 | Wu et al. |
| 4,963,297 A | 10/1990 | Madden |
| 4,963,362 A | 10/1990 | Rahman et al. |
| 4,990,337 A | 2/1991 | Kurihara et al. ........... 424/427 |
| 5,000,959 A | 3/1991 | Iga et al. |
| 5,002,940 A | 3/1991 | Geller et al. ............... 424/178 |
| 5,025,004 A | 6/1991 | Wu et al. |
| 5,110,475 A | 5/1992 | Rössling et al. |
| 5,152,923 A | 10/1992 | Weder et al. |
| 5,283,067 A | 2/1994 | Geller et al. ............... 424/489 |

FOREIGN PATENT DOCUMENTS

| | | |
|---|---|---|
| EP | 0 169 618 | 1/1986 |
| EP | 0 220 153 | 4/1987 |
| EP | 0 220 797 | 5/1987 |
| EP | 0 261 802 | 3/1988 |
| EP | 0 274 431 B1 | 7/1988 |
| EP | 0 276 911 | 8/1988 |
| EP | 0 296 845 | 12/1988 |
| EP | 0 361 928 | 4/1990 |
| EP | 0 391 369 | 10/1990 |
| EP | 0 429 428 | 5/1991 |
| GB | 1 532 993 | 2/1976 |
| GB | 2 200 048 | 7/1988 |
| GB | 2 201 089 | 8/1988 |
| GB | 2 230 440 | 10/1990 |
| JP | 63072678 | 2/1988 |
| WO | WO 88/06438 | 9/1988 |
| WO | 88/06438 | 9/1988 |

OTHER PUBLICATIONS

S. Benita, et al., vol. 73, No. 12, 1751–1755 (1984).
Bensouda, et al,. Lab de Phar. Galén. et de Biophar., 241–250, France (undated). (+Translation).
Chem. Abst., 125896h, vol. 106, 399 (1987).

(List continued on next page.)

Primary Examiner—James M. Spear
(74) Attorney, Agent, or Firm—Gabriel Lopez (57) ABSTRACT

Particles of a substantially water insoluble biologically active substance, such as Cyclosporin, are loaded with a charged glyceryl ester as an electrostatic stabilizer which imparts to the particles a zeta potential and having an active substance:stabilizer weight ratio of 1:1 to 400:1 and an average particle diameter of 1 nanometer to 10 micrometers. Compositions having such particles are found to be useful delivery systems.

46 Claims, 4 Drawing Sheets

OTHER PUBLICATIONS

Chem. Abstr., 173227x, vol. 110, 776 (1989).
Chem. Abstr., 2182575, vol. 113, 394 (1990).
Davis and Illum, Acta Pharm. Technol., 32 (1), 4–9 (1986).
D. Forster, et al., J. Pharm. Pharmacol., 40:325–328 (1988).
Hunter, Zeta Proteins in Colloid Science, 238–245 + 310–313, Academic Press (1981).
Ilum, et al., Int. of Pharm., vol. 29, 53–65 (1989).
A.S. Janoff, "Current Topics in Infectious Diseases and Clinical Microbiology, vol. 2", Jackson et al. eds., 145–151 (1989).
A.S. Janoff, et al., J. of Liposome Res., vol. 3 (3), 451–471 (1993).

Levy and Benita, Internal. J. of Pharma., vol. 54, 103–112 (1989).

Loosli, et al., Helvetica Chimica Acta, vol. 68, 682–704 (1985).

H. Steffen, Jour. Galéni. de Saint Rémy–de–Provence, 45–53 (1988).

Müller and Heinemann, Deutsche Apotheker Zeitung, vol. 129, No. 41, 2188–2193 (1989). (+ Translation).

C. Washington, et al., Internat. J. of Pharma., vol. 46, 25–30 (1988).

PHARMACEUTICAL COMPOSITIONS COMPRISED OF STABILIZED PEPTIDE PARTICLES

This is a continuation of Ser. No. 09/257,126, Feb. 25, 1999, abandoned, which is a continuation of Ser. No. 08/137,088, Oct. 8, 1993, abandoned, which is a 371 of PCT/EP92/00862, Apr. 16, 1992.

This application is a 371 of PCT/EP92/00862 filed Apr. 16, 1992.

This invention relates to particles of biologically active substances that are electrostatically protected against coagulation when they are dispersed in water, e.g. producing colloids, and pharmaceutical compositions containing them.

Biologically active substances are understood to include those active substances, i.e. pharmacologically active substances, which may be used in medicine as medicaments or in the agricultural industry e.g. as pesticides. The term "biological compositions" therefore also includes compositions which are employed in the agricultural industry. However, the invention relates in particular to pharmaceutical compositions for medicinal usage.

Colloids produced on dispersing the particles may have in general a particle size of between 1 and 10000 nanometers (=0.001 to 10 micrometers). These colloidal particles in compositions of the present invention are believed to consist only of active substance in amorphous form. The small size of the particles, especially less than 2 micrometers, enables intravenous application of the colloidal drug particles to take place without any danger of blocking the finest blood capillaries.

The colloidal state in itself is generally regarded as unstable and liable to collapse since this finely-dispersed state is associated with a large surface area. The colloidal system attempts to;reduce the surface area in the dispersion medium by coagulation,: e.g. aggregation, flocculation or crystallization. Addition of stabilizers is necessary to prevent this.

Basically, there are two known principles of stabilization. The first is steric stabilization. Polymer molecules are adsorbed on the surface of the particles and prevent aggregation or flocculation through their chains which reach into the dispersion medium.

The second principle is based on charging particles positively or negatively and on the resulting reciprocal repulsion of the particles. The stabilizer is charged and contains a lipophilic moiety which is suitable for adsorption onto the lipophilic surface of the particles. Since the potential prevailing at the particle surface is poorly accessible for technical measurement, the so-called zeta potential has become is a well known characteristic used e.g. to indicate the stability of electro-statically stabilized particles. The zeta potential of an electrostatically stabilized particle may be regarded as the electric potential prevailing at its boundary surface, corresponding to a layer at a certain distance from the particle up to which electrolyte ions in solution are brought or from which they are removed by thermal motion.

The zeta potentials may be determined in conventional manner, e.g. as described in example 3 hereinafter.

The present invention provides in one aspect particles of a substantially water insoluble biologically active substance having on the surface thereof charged glyceryl ester, the particles having an active substance: ester weight ratio of from 1:1 to 400:1.

In another aspect the invention provides pharmaceutical compositions comprising particles of a biologically active substance which is very poorly soluble in water and which are free from polymeric or cross linked nucleus, wall or matrix material, but loaded with a negatively or positively charged glyceryl ester as an electrostatic stabilizer which imparts to the particles a zeta potential of −1.5 to −100 or from +1.5 to +100 mV when in an aqueous 0.01 molar KCl solution, the particles having an active substance: stabilizer weight ratio of 1:1 to 400:1 and having diameters of 1 nanometer to 10 micrometers when measured in a liquid medium.

The present invention also provides a process for the production of particles according to the invention which comprises mixing a) an organic solution containing 1 to 100 mg/ml pharmacologically active substance and the glyceryl ester or electrostatic stabilizer and b) an aqueous medium are under conditions such that in the corresponding mixture the weight ratio of active substance to ester or stabilizer corresponds to that given above.

In a further aspect the present invention provides a process for the production of a pharmaceutical composition according to the invention wherein in a first step the particles are produced, with subsequent isolation of the resultant colloidal particles.

The glyceryl esters preferably have organic and inorganic acid moieties. The organic acid moiety is preferably of a fatty acid. The inorganic acid moiety is preferably derived from a polybasic acid, e.g. phosphoric acid. Additionally, the glyceryl esters may contain amino residues, e.g. amino alcohol ester residues, or hydroxyl residues, e.g. glycerol.

The organic acid moiety is the lipophilic moiety of the glyceryl ester; the inorganic acid moiety may, if in salt form, give the glyceryl ester molecule its negative charge; the amino moiety, if present, may, if quaternized, give the glyceryl ester molecule a positive charge.

A preferred class of glyceryl esters are the negatively and positively charged phospholipids.

The biologically active substances are preferably those which may be employed in medicine.

Preferably their water solubility is less than 1 part by weight of substance per 1000 parts by volume of water (=0.1% or $1^{mg}$/ml at room temperature).

Such substances are classified according to USP XXII (1990) as very poorly (slightly) soluble.

The water solubility is preferably at least 1 part by volume of substance per 10000 parts by volume of water (=0.01% or $0.1^{mg}$/ml).

The active substances may belong to any of a wide variety of chemical classes. One example of an active substance are the imidazoles. Another Example is FK 506. This compound has been described in Merck Index, Eleventh Edition, Appendix, A5. Analogues of FK 506 are also generally known. The active substances are preferably very poorly soluble peptides, especially cyclopeptides, such as those having cyclosporin structure, such as the cyclosporins, especially those having a water solubility of at most 400, especially at most 40, micro-grams per ml of water. The cyclosporins comprise a known class of pharmacologically active substances, which are described extensively together with their medicinal uses in the literature see e.g. GB 2,222,770 A (the contents of which are incorporated by reference). Preferred cyclosporins are cyclosporin A (=ciclosporin), cyclosporin G (see Example 3), cyclosporin D and the other cyclosporins mentioned in Example 3.

BRIEF DESCRIPTION OF THE DRAWINGS

FIG. 1 illustrates a drying process for the particles of the invention.

FIGS. 2 and 3 represent comparative results showing distribution patterns of cyclosporin A following IV administration of the commercial KZI solution and of the new colloidal particles of cyclosporin, in various organs of the body.

The following is background to the present invention especially as regards stabilization of colloidal particles:

According to "Zeta Potential in Colloid Science", by Robert J. Hunter, Academic Press, 1981, colloidal silver iodide particles, which carry a negative or positive initial charge due to excess adsorbed iodide or silver ions, acquire a zeta potential of up to about +90 mV (page 245) with positively charged surface-active agents such as dodecyl pyridinium bromide, or a zeta potential of up to about –200 mV (page 311) with negatively charged surfaceactive agents such as sodium dodecyl sulphate.

However, these products cannot be regarded as biological compositions. Silver iodide is not employed as a pharmacologically active substance and the surface-active agents used are not suitable for pharmaceutical purposes in medicaments, e.g. because of their strong haemolytic activity and because of toxicological considerations.

In U.S. Pat. No. 4,826,689 it is mentioned in passing that a zeta potential threshold may have to be exceeded to prevent colloid particles such as those of pharmacologically active substances from coagulating; however, this threshold is not numerically stated.

British patent application GB 2,200,048 A, discloses that intravenous application of colloidal drug particles is possible. An injection induces an immediate pharmacological effect which corresponds to that of a solution of the active substance. According to this application, in order to be able to produce stable, dry, sterically stabilized colloidal drug particles of the active substance e.g. cyclosporin A, which can be resuspended in liquid, e.g. aqueous media, it was preferred to add a peptizer such as citric acid, as well as a polymeric stabilizer such as gelatin, and the carrier such as mannitol.

Citric acid, which is an effective peptizer because of its negative charge, has a lipophilic proportion which is too small for it to be absorbed at the lipophilic drug particles, and cannot therefore be considered to function as an electrostatic stabilizer. Instead, citric acid shifts the pH of the solution to the range in which the gelatin employed has its isoelectric point and can not offer electrostatic stabilization.

Especially where intravenous application of larger amounts of colloidal cyclosporin A particles takes place, the required amount of citric acid is released and exceeds the buffer capacity of the blood, so that the pH value of the blood is shifted towards the acidic range. For this reason, it would be advantageous to dispense with the peptizer such as citric acid. In addition, a large amount of gelatin may be necessary.

The particles according to the present invention do not require any kind of peptizer addition, for they are stabilized by minimal additions of negatively or positively charged glyceryl esters as electrostatic stabilizers, e.g. lecithin, and have higher stabilizing power than those described in the above patent specification. They are stabilized in particular by charged phospholipids, such as natural lecithin or lecithin fractions. These substances thus belong to the class of electrostatic stabilizers. Generally only the charged components thereof contribute to the stabilization of the particles. This is evidenced by the fact that when using highly pure, uncharged lecithin components, immediate flocculation occurs as a result of insufficient stabilization.

It is possible to differentiate the particles according to this invention from liposomes which similarly contain lecithin because of the completely different ratio of active substance/excipient. While liposomes have a ratio of active substance:excipient of at most 1:2 (=0.5:1), when using phosphatidyl glycerin to stabilize colloidal particles according to the present invention, a ratio of active substance: excipient of 1:1, such as 50:1, is sufficient. The difference resides in the fact that, in the case of liposomes, the phospholipids are used to build up the lipid double layers, which requires a relatively high amount of lecithin.

On the other hand, the phospholipids of the particles of the invention are adsorbed in a e.g. monomolecular layer on the surface and therefore less lecithin molecules are sufficient to stabilize the particles.

The sizes of particles according to the present invention and of nanoparticles having the same order of magnitude. They can be differentiated from each other in that, as is known, the latter are made up of modified polymer matrices or possess a polymer coating. The active substance in the nano-particles either is dispersed molecularly in the polymer matrix, or the active substance or its solution is encased by, preferably water insoluble, polymeric or cross-linked wall material. The aim of intravenous application of nano-particles is, as with liposomes, normally to delay release of the active substance from the colloidal carriers. Following intravenous injection of nano-particles or liposomes, they are taken up increasingly into certain areas of the body, namely the Reticulo-Endothelial-System (RES). Macrophages, which identify the particle coatings as foreign to the body, are responsible for this process. The active substance is therefore distributed in the same way as the colloidal carrier in the body and not as a solution of the active substance. This has led to considerable setbacks in the use in particular of nano-particles. In contrast to this, when the colloidal particles according to this invention are injected intravenously, they are surprisingly distributed in the same way as a solution of the active substance, due to the fact that even substances which are considered insoluble still have a certain residual solubility, so that when a certain amount is injected into the blood supply as a colloidal solution, it is distributed therein and dissolved as a molecular dispersion.

Preferred embodiments of the invention are compositions having electrostatically stabilized particles which are free from polymeric or cross-linked wall or matrix material, with a weight ratio of active substance:stabilizer of 1:1 to 200:1. The diameter of the drug particles is preferably at most 1, especially at most 0.3, particularly at most 0.2 micrometers.

The invention especially provides pharmaceutical compositions having particles of a biologically active substance which is very poorly soluble in water, such as a cyclosporin or FK 506 or an analogue thereof, with an electrostatic stabilizer, consisting of negatively or positively charged, natural or synthetic phospholipids:, especially a natural lecithin. Such lecithins may be of vegetable origin, e.g. from soya beans, rape or sunflower seeds, or may stem from animal sources, e.g. eggs or cerebral substance.

The colloidal particles may be electrostatically stabilized with partially or fully synthetic phospholipids, or mixtures of these phospholipids, or mixtures of these phospholipids with natural lecithins. For the stabilization of the colloidal particles the above-mentioned stabilizers comprise at least partly of negatively or positively charged phospholipids.

According to example 3 of PCT application WO 88/06438, colloidal particles of the active substance cyclosporin A, which is very poorly soluble in water, together with a stabilizer are prepared in a weight ratio of active substance:stabilizer 2:1 and with diameters of about 1.0 micrometers.

A solution of the cyclosporin and the stabilizer in absolute ethanol and polyethylene glycol 400 is injected in dextrose containing water leading to a suspension of stabilized colloidal particles.

However, the stabilizer consisting of phosphalidylcholine does not have electrostatically stabilizing activity, since it is a zwitterion and thus does not offer any contribution towards the zeta potential in the said millivolt range according to the invention. The stabilizer contains a portion of charged, not soluble phospholipids. To enable its dissolution in the mentioned organic solution the stabilizer is desalted. This means (see page 14, lines 28–32 of the above reference) that its charged moiety is converted into its soluble free acid or base and its charge is taken away. The cyclosporin suspension's distribution of particle sizes is, not very favourable. Some particles having a diameter of up to 40 micrometers have been found, which are too large for intravenous application. For such an application, only particles of up to 5–7 micrometers as the upper limit are considered as safe. According to EP 0,391,369 A2, an oil-in-water emulsion of a pharmacologically active substance, such as a cyclosporin, is formed. The oil droplets of the emulsion contain the lipophilic active substance in a dissolved state. Phospholipids at the surface of the droplets stabilize the emulsion against coagulation of the droplets. The phospholipids may be electro-statically charged, and with other charge carriers that are present, transfer their charge to the oil droplets, which are measured as zeta potentials.

However, the oil droplets contain no active substance in colloidal form.

A disadvantage of this emulsion is the high proportion of oil and other excipients, in contrast to the colloidal drug compound particles according to the invention. An acceptable spray-dried product of loose constitution (e.g. dispersable) is not possible because of the presence of the oils.

One electrostatic stabilizer for the particles according to the invention is preferably natural lecithin which, apart from zwitterionic phospholipid, also comprises e.g. 3 to 60%, in particular 5 to 35, especially 10 to 25%, by weight of positively or preferably negatively charged phospholipids, such as phosphatidyl-glycerol, phosphatidyl-inosite, phosphatidylserine, phosphatidic acid and their salts. In particular, the stabilizer may also be a phospholipid e.g. a negatively charged phospholipid obtained by extraction from natural lecithin, as well as such, obtained partially or completely by synthesis.

The weight ratio of active substance to stabilizer is, as said before, preferably between 1:1 and 200:1, but in particular between 10:1 and 60:1, especially between 30:1 and 50:1.

The particles disclosed in PCT application WO 88/06438 have in example 4 a weight ratio of active substance:stabilizer of below 1:1, e.g. 1:2, and thus lie outside of the range of weight ratios according to the invention.

According to page 19, lines 27–35, the active substance: stabilizer weight ratio is a critical factor for distinguishing whether simple colloid particles or liposomes exist, and the limit is a ratio of 1:1. Below this limit, they exist as liposomes. The particles of this Example 4 are thus liposomes. The stabilizer consists of desalted egg phosphatide, i.e. mainly of zwitterionic phosphatidylcholine, which as mentioned above, does not offer any electrostatically stabilized particles in the millivolt range according to the invention.

Preferred stabilizers for the particles according to the invention are negatively charged pure substances, such as phosphatidyl-glycerol, which when used in a very small quantity enable the particles to stabilize, and surprisingly create a smaller particle size than the natural, pharmaceutically acceptable lecithins. In general, the particles according to the invention surprisingly are produced with smaller diameters than those of the sterically stabilized particles. In addition, the above-mentioned pure substances result in a higher zeta potential, and accordingly also a greater repulsion of the particles and thus improved stability when compared with the natural lecithins. From an analytical perspective, these pure phospholipids may be regarded as clearly defined substances which simplify detection of the degradation of active substances in. the final formulation. Natural lecithins consist of a number of substances which make it difficult to recognize small amounts of degradation products.

Colloidal particles similarly form part of the invention, preferably those which have a concentration of 0.01 micrograms to 20 mg, in particular up to 6 mg, especially 5 mg of a cyclosporin or FK 506 or analogue thereof per ml of a liquid medium. The pharmaceutical compositions with solutions of particles are preferably produced in aqueous media. As is known per se, the particles may be isolated by centrifuging or by filtration, but the particles then may form a compact, poorly re-suspendable cake. For this reason, it is advantageous to obtain the particles in a re-suspendable form by lyophilization or in particular by spray-drying.

The electrostatic stabilizers, although preferred to the steric stabilizers, may be insufficient to allow stability during concentration of the colloidal dispersion e.g. during lyophilization or spray-drying, since the distance between the particles may be so small that van der Waals-attracting forces begin to play a role. It is therefore preferable to use a carrier which keeps the particles apart during evaporation of the liquid. In the preferred embodiment, the dispersion medium contains 1 to 20, especially 4 to 6%, by weight of this carrier.

Preferred embodiments of the invention include pharmaceutical compositions with particles, stabilized electrostatically with one of the above-defined stabilizers and with a carrier which serves as a basis for spray-drying. These carriers may be conventional carriers, e.g. as described in GB-PS 15 16 348. Suitable carriers include all those which are capable of keeping apart the colloidal drug compound particles during the concentration process, to prevent their coagulation and thus to stabilize them: e.g. dextran, saccharose, mannitol, glycine, lactose, polyvinyl pyrrolidone. The carrier is preferably a sugar or a sugar alcohol.

To improve moistening of the carrier in the final dry product, a surfactant can be added.

According to U.S. Pat. No. 4,826,689, a poloxamer is used as a steric stabilizer to prevent coagulation of colloid particles of pharmacologically active substances. The poloxamers are polyoxyethylene-polyoxypropylene block copolymers. As they are hydrophilic, these products can also be employed as surfactants to impart hydrophilic properties to hydrophobic particles.

According to Int. J. of Pharm. 29 (1986) 53–65 radioactive marked microparticles having a nucleus of polystyrene and a diameter of 60 nm and being stabilized partially electrostatically and partially sterically with egg lecithin or sterically with poloxamers or loaded with secretary immunoglobulin A (SIgA) molecules on their surface are injected into rabbits to investigate their distribution among the organs in the body and their elimination by macrophages.

In contrast the present invention is not concerned with the stabilization of a polymeric nucleus materials or loading with molecules of active substances. Instead solid biologically active substance particles are stabilized.

During spray-drying, the particles may be subjected to hydrophobization of the surface of the resultant powder particles. Thus preferably a surface-active substance which promotes wetting is added to the spray solution. This substance may be a surfactant, e.g. polyoxyethylated castor oil, or in particular a polymeric surfactant of the poloxamer type. The poloxamer effects a reduction in the zeta potential, depending on concentration, perhaps through (partial) expulsion of the electrostatic stabilizer, or through (partial) screening of the electrostatic stabilizer on the colloid particles. A zeta potential of a minimum −10 or +10 mV, caused by the electrostatic stabilizer, can thus be reduced to −1.5 or +1.5 mV, respectively. The concentration of surface-active substance in the aqueous dispersion medium is in particular 0.001 to 1, especially 0.01 to 0.1, especially 0.03 % by weight.

The biological compositions according to the invention may be produced in conventional manner. They are preferably produced according to the process of the invention, wherein separate currents of liquid of a) an organic solution, e.g. ethanol, which contains the active substance, e.g. a cyclosporin or FK 506 or analogue thereof, in a concentration of 1 to 200 mg/ml, as well as the electrostatic stabilizer and b) an aqueous dispersion medium, which may contain the carrier and the surface active substance, are brought together so that in the resultant colloid-disperse system the weight ratios of active substance to stabilizer, or of carrier and surface-active substance to medium correspond to the ranges mentioned above. The colloidal particles are thus formed by mixing the two liquids as quickly as possible, so that the stabilizer migrates within the border surface around the particles. By using natural lecithin as the stabilizer, the surface of the colloidal particles is rapidly stabilized, which can be detected as soon as a zeta potential of below −10 mV is measured which scarcely changes with time. If however a pure, negatively charged phospholipid is used, then the zeta potential shifts to more negative values until, after one day, a constant value is be obtained (see example 3).

The separate currents of liquid are preferably brought together by continuous mixing, in particular in a static mixer. Static mixers may be comprised of baffle plates without movable parts, which are incorporated into a pipe system, where homogenization or mixing of the currents is attained. This principle is used for example for mixing liquids.

Lyophilization of the colloidal particles formed in the static mixer often leads to changes in the size of the particles following reconstitution to a colloidal solution. New and surprising is, inter alia, that, when prepared by spray-drying, the electrostatically stabilized colloidal particles according to the invention may be rendered more stable in storage than the sterically stabilized colloid particles. The high temperature and the short drying time resulting therefrom minimise changes in particle size. Dry powders which are stable in storage and have been produced in this way may be re-suspended to afford the original particle size, which on average is smaller than that of reconstituted, sterically stabilized particles.

Thus, the invention also provides pharmaceutical compositions with spray-dried, electrostatically stabilized particles. The pharmaceutical composition may contain pharmaceutical excipients, e.g. additional to those employed in the production of the particles.

Such carriers can include disintegrants, lubricating agents etc. such as those disclosed in the Examples hereinafter.

In the spray-dried form e.g. with cyclosporin, the weight ratio of active agent to carrier is preferably 1:5 to 1:200, in particular 1:10 to 1:40, especially 1:20.

Similarly, the invention provides pharmaceutical compositions with electrostatically stabilized colloidal particles, which after being formed in a static mixer, are converted into powder form by spray-drying.

The invention in particular provides pharmaceutical compositions with spray-dried, electrostatically stabilized, colloidal particles, of e.g. cyclosporins, FK 506 or analogues thereof, in powder form, with an average particle size of the powder of 1 to 500 micrometers, especially 3 to 50 micrometers, measured in the dry state and with an average particle size of the colloidal particles contained therein of 0.1 to 10, preferably 0.15 to 0.5 micrometers.

The pharmaceutical compositions containing the electrostatically particles are used according to the invention as medicaments.

The invention thus provides pharmaceutical compositions which contain the particles in the form of e.g. capsules, tablets, solutions for drinking, suspensions, powders, salves, gels, creams or suppositories.

The spray-dried powder may be employed, especially after re-suspending, as a solution for drinking, as a pulmonary inhalation solution or as a parenteral application liquid. In powder form, the particles may be used for nasal or pulmonary application. Together with pharmaceutical excipients, the spray-dried powders may be filled into capsules or pressed into tablets, and are then suitable for oral application or as capsules also for pulmonary application. When processed into suppositories according to the invention, the powders can be applied rectally.

The compositions according to the invention are useful for biological, e.g. medicinal indications and at dosages, at which the active substances contained therein are e.g. therapeutically effective, as indicated by standard biological tests, e.g. clinical and bioavailability trials.

Surprisingly, increased bio-availability of the active substance was established in the oral compositions containing electrostatically stabilized cyclosporin particles according to the invention. Oral compositions with increased bioavailability and also a rapid increase of the cyclosporin concentration in the blood after administration are those of Examples 4, 5 and 6.

The invention thus also provides a method for the administration of a pharmacologically active substance to a subject requiring it, which method comprises administering to said subject an effective amount of a pharmaceutical composition according to the invention.

The invention additionally provides a) a pharmaceutically composition according to the invention, containing a cyclosporin, for use as an immuno- suppressant or for the treatment of autoimmune diseases or inflammation conditions or diseases having an autoimmune component or parasitic infections or attacks and b) a method of effecting immunosuppression or for the treatment of autoimmune diseases or for the treatment of inflammatory conditions or diseases having an autoimmune component or parasitic infections or attacks in a subject in need thereof, which method comprises administering to said subject an effective amount of a pharmaceutical composition of the invention.

In the following examples, the particles according to the invention are produced or employed.

EXAMPLE 1

Continuous Production and use of the Pharmaceutical Compositions having Electrostatically Stabilized Drug Compound Particles 1. Preparation of the Solutions a. Aqueous Solution:

0.3 g of poloxamer 188 (pluronics F-68$^R$) containing 75 ethyleneoxy and 30 propyleneoxy groups, and 100.0 g of lactose are dissolved in distilled water to make up 1 l, and transferred through a sterile filter with a pore size of 0.2 micrometers into a sterile tank.

b. Organic Solution:

3.00 g of cyclosporin A and 0.06 g of palmitoyl-oleyl-phosphatidyl-glycerol are dissolved in 60 ml of absolute ethanol, and transferred through a sterile filter with a pore size of 0.2 micrometers into a sterile tank.

2. Production of the colloidal drug compound particles

Figure 1:
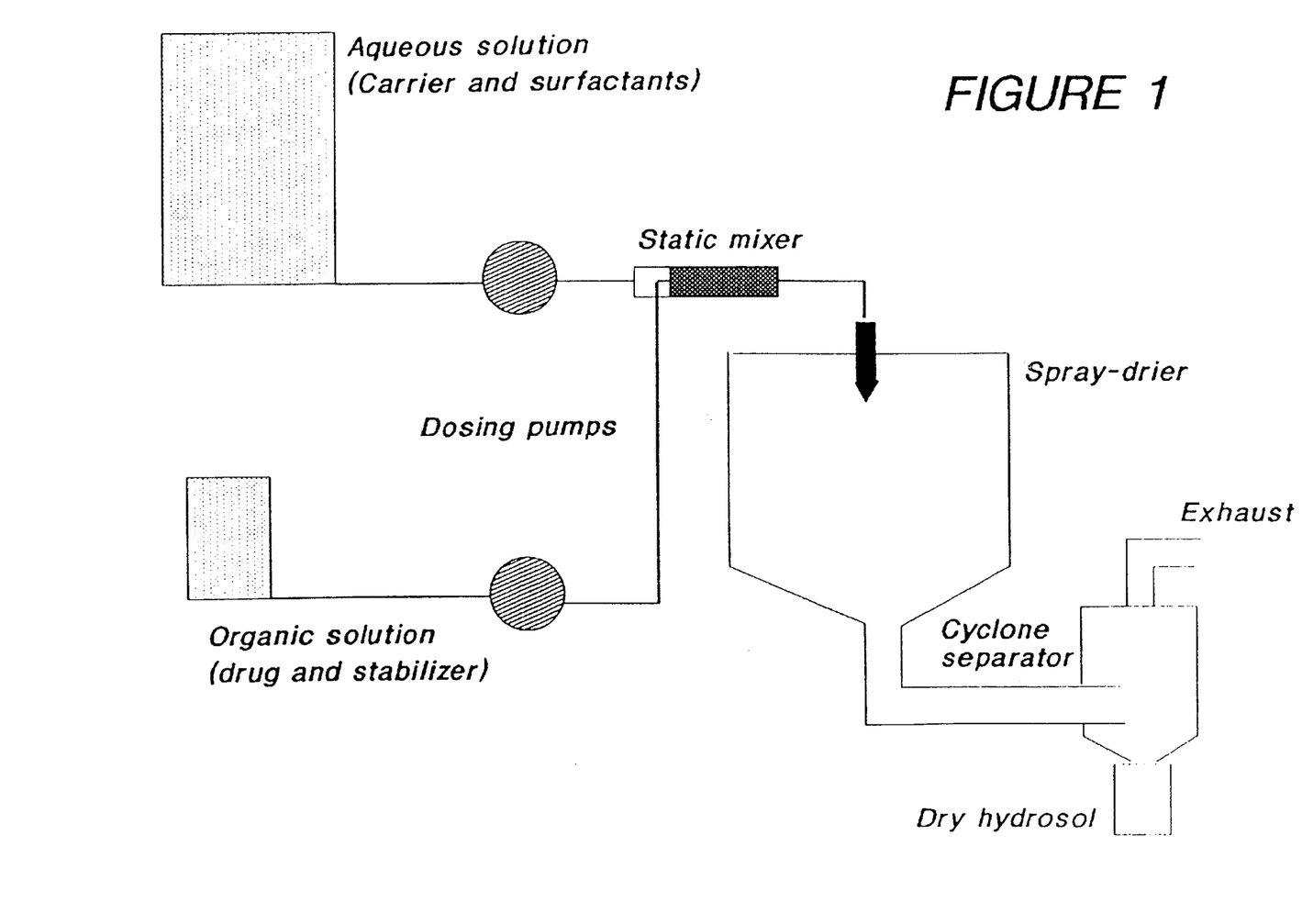

FIG. 1 shows the continuous production and drying of colloidal particles of cyclosporin A.

The tanks with the aqueous solution and the organic solution are separately connected to measuring pumps by sterile hoses.

The solutions are fed by the two pumps through sterile hoses to a static mixer (Sulzer, 10 mixing elements, diameter of each element 3.4 mm). Other static mixers may be used, e.g. that of Kenics. The aqueous solution is pumped through the static mixer at a rate of 9.4 ml/minute. The organic solution is injected coaxially into the aqueous phase directly before the first mixing element, at a rate of 0.6 ml/minute. In the static mixer, the two liquids are combined, and as a result of intensive mixing, colloidal particles of cyclosporin A are formed.

The particle size of the colloidal particles, measured by laser beam scattering, is 80 nanometers with a standard deviation of 15 nm.

3. Drying of the Colloidal Drug Particles

As illustrated in FIG. 1, the resultant colloidal particles of cyclosporin A are fed on-line to a two-component nozzle which is suspended in the drying tower of a spray drier (Niro). At an atmospheric pressure of the spray of 1.5 bar, the sol of the colloidal drug compound particles is dispersed into fine droplets and dried at an air supply temperature of 150° C. The air supply is introduced through a 0.2 micrometer sterile filter at the entrance to the drier. Separation of the dry form takes place in a cyclone. The air temperature here is still ca. 75° C. The outgoing air is removed through a blower. The average particle size of the resultant powder is 38 micrometers. The content of cyclosporin A powder is 29.8 mg/g powder.

4. Application of the Dry form of the Colloidal Drug Compound Particles

The dry form of the colloidal particles can be filled into vials, and after adding water produces a colloidal system again, with a particle size of 120 nanometers and a standard deviation of 65 nm. These re-dispersed colloidal particles of cyclosporin A are administered parenterally e.g. intravenously.

Alternative applications are:

Filling into capsules or pressing into tablets, optionally employing further excipients.

Direct use or re-dispersement of the colloidal drug compound particles, with subsequent use as a solution for drinking. These forms are suitable for oral application.

Filling into an inhaler, with subsequent nasal or pulmonary application. Also possible is re-dispersement in water and pulmonary application via nebulizers.

Incorporation into a salve base or creme formulation for subsequent dermal application.

Incorporation into a suppository base for subsequent rectal application.

EXAMPLE 2

Use of the Pharmaceutical Compositions with the Colloidal Particles in an In-vivo Test The distribution of colloidal particles of cyclosporin A in the organism following intravenous application was compared with that of the commercial cyclosporin A concentrate for infusion (SANDIMMUNE) (KZI), diluted with isotonic glucose solution, following intravenous application to rats. For this test, detection was effected using radioactively labelled active substance. In all organs, the distribution of the colloidal particles of cyclosporin A according to the invention corresponded to that of the KZI solution.

This indicates that the colloidal particles, in contrast to nano-particles (e.g. of polymethacrylates or polycyanoacrylates) are not accumulated in certain organs, but are distributed as a micellar solution of the active substance.

Figure 2:
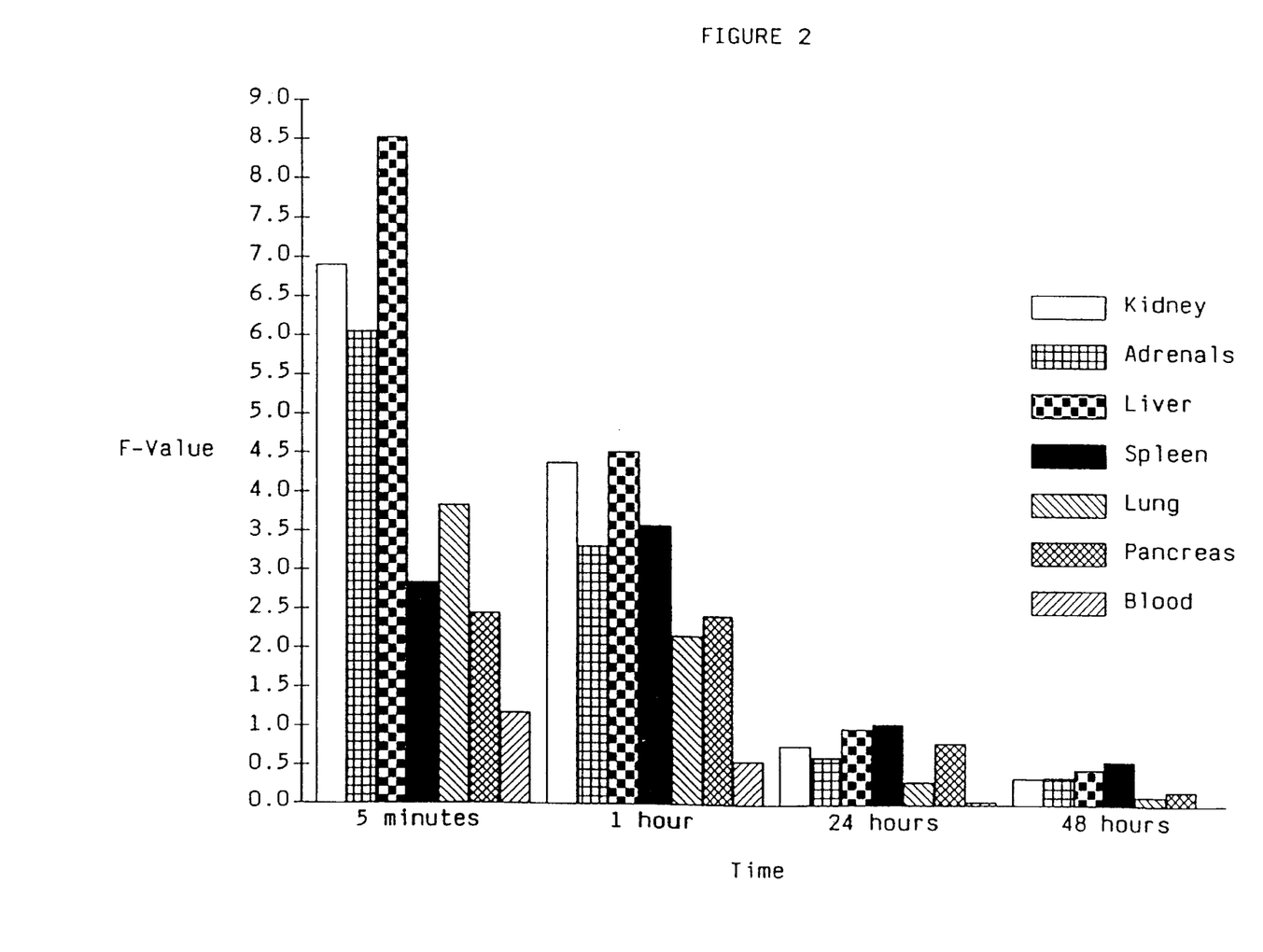
Figure 3:
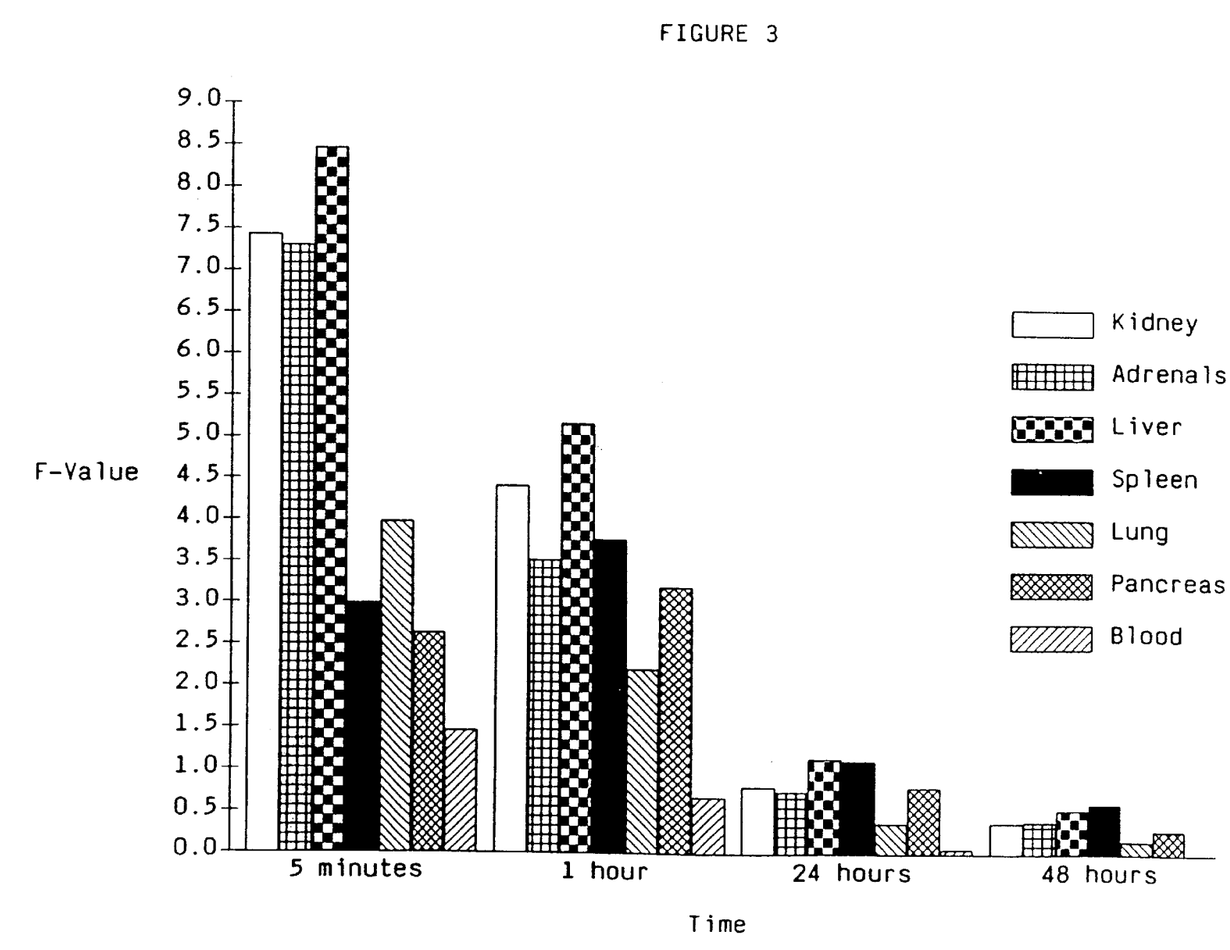

FIGS. 2 and 3 show the distribution of cyclosporin A following intravenous administration of the commercial KZI solution and of the new colloidal particles of cyclosporin, in the various organs of the body, measured by "liquid scintillation counting" following removal and dissolving of the organs. Distribution of the radioactively labelled active substance was determined after 5 minutes, 1, 24 and 48 hours.

The details given in the figures are in F-values. The F-value is defined as the concentration per g organ or blood, divided by the dosage applied per g of body weight.

Distribution Pattern in Rats' Bodies of Colloidal Particles of Cyclosporin A Compared with the Distribution of the Commercial Concentrate for Infusion (KZI)

Colloidal particles of cyclosporin A:

12.01 mg of unlabelled cyclosporin A and 0.345 mg of [$^3$H]-cyclosporin A and 0.0345 mg of phospholipon 80 are dissolved in 0.25 ml of absolute ethanol. Using e.g. an Eppendorf Varipette, this organicsolution is mixed with stirring into 4.2 ml of aqueous solution (5.0 g of mannitol dissolved in 94.7 g of distilled water). Colloidal particles are produced. The final volume is 4.45 ml.

Cyclosporin A-KZI:

12.57 mg of cyclosporin A and 0.331 mg of [$^3$H]-cyclosporin A are dissolved on a magnetic stirrer in 233.9 mg of KZI medium (650.0 mg of Cremophor EL (BASF)= poly-(35)-oxyethylated castor oil) and 278.0 mg of absolute ethanol are mixed and produce a viscous solution).

The solution is diluted with an isotonic glucose solution to give a final volume of 4.2 ml.

0.3 ml of each of the two above formulations is applied to the femoral veins of male Kfm WIST rats. At a weight of about 200 g, this corresponds to the average dosage normally employed of 4.5 mg cyclosporin A/kg body weight. The radioactive dosage was 200 microCi/kg except for the animals for whole body auto radiography, in which the radioactive dosage amounted to 2000 microCi/kg body weight. The distribution pattern of the two formulations in the body was determined after 0.08, 1, 24 and 48 hours with one animal per time, using whole body auto radiography. In addition, the distribution pattern of radioactivity in the individual organs was measured after dissolving by "liquid scintillation counting" using groups of two rats.

EXAMPLE 3

Zeta Potential Measurements

All zeta potential measurements were made with a Malvern Zetasizer III, Malvern Co., Malvern, GB. The concentration of active substance was 1 mg/ml. The dispersing medium used was 0.01 molar potassium chloride solution, which provides a satisfactory conductivity. The conditions of the measurements were as follows:

Measuring cell: AZ 4, Malvern Co., Malvern, GB

Electrolyte: 0.01 m potassium chloride solution

Temperature: 25° C.

Voltage: 120 V

Measuring angle: 90°

Active substance: content 1 mg/ml

Zeta potentials and particle sizes of colloidal drug compound particles.

|  | Zeta potential | | particle size | |
|---|---|---|---|---|
|  | Prodn. | 24 h. | Prod. | 24 h. |
| ciclosporin/POPG 50:1 | −24.7 mV | −44.4 mV | 97.8 nm | 121.5 nm |
| ciclosporin/POPG 40:1 | −26.5 mV | −47.9 mV | 84.8 nm | 110.2 nm |
| ciclosporin/POPG 30:1 | −24.0 mV | −46.4 mV | 80.6 nm | 109.3 nm |
| ciclosporin/POPG 20:1 | −24.9 mV | −48.4 mV | 83.8 nm | 109.0 nm |
| ciclosporin/POPG 10:1 | −24.3 mV | −47.9 mV | 83.6 nm | 106.6 nm |
| ciclosporin/PL 80 30:1 | −16.0 mV | −17.0 mV | 158.3 nm | 161.3 nm |
| ciclosporin/PL 80 20:1 | −16.5 mV | −18.0 mV | 141.9 nm | 145.8 nm |
| ciclosporin/PL 80 10:1 | −16.8 mV | −18.4 mV | 139.4 nm | 142.9 nm |
| cyclosporin G/ 10:1 PL 80 | −21.0 mV | −23.0 mV | 138.8 nm | 144.9 nm |
| [3'-desoxy-3'-oxo-MeBmt]$^1$-[Val]$^2$-ciclosporin [1]/ PL 80 10:1 | −20.9 mV | −22.8 mV | 136.2 nm | 144.5 nm |
| [0-(2-hydroxyethyl)-(D)-Ser]$^8$-ciclosporin [2]/ PL 80 10:1 | −21.3 mV | −22.9 mV | 265.4 nm | 790.3 nm |
| FK 506/PL 80 10:1 | −22.9 mV | −22.9 mV | 235.2 nm | 495.2 nm |

POPG = palmitoyl-oleyl-phosphatidyl-glycerol
PL 80 = phospholipon 80 (Natterman), with 80% by weight of uncharged phosphatidylcholine and 10% of negatively charged phospholipids
Footnote:
[1] Described in EP 0 296 122 A2 as cyclosporin 1.38 (see also example H)
[2] Described in EP 0 414 632 A2, Example 2.

The particles were produced in analogous manner to that described in example 1.

The zeta potential generally rises as production proceeds. After 24 hours production a constant value is reached. The zeta potential increase with pure negatively charged phospholipids is greater than with phospholipid mixtures having uncharged parts of molecules.

With positively charged phospholipid molecules the zeta potential is positive. Accordingly, the absolute value of the zeta potential (i.e. without taking into consideration the negative or positive sign of the potential) is decisive. A mixture of negative and ppositive stabilizer molecules on the surface of the colloid particles leads to (partial) neutralization of the electrostatic surface charge and allows the zeta potential to drop in absolute value. However, as long as the potential of the mixture lies within the absolute range of 1.5 to 100 mV, the mixture is one according to the invention.

Influence of Poloxamer 188 on the Zeta Potential of Colloidal Drug Compound Particles Drug concentration was 1 mg/ml. Poloxamer solutions at various concentrations were used as the dispersing media, respectively with 0.01 molar potassium chloride to guarantee conductivity. Poloxamer 188 (e.g. Pluronic $^R$ F-68) containing 75 ethyleneoxy and 30 propyleneoxy groups.

Zeta potentials and particle sizes

| Zeta potentials and particle sizes | | | | |
|---|---|---|---|---|
|  | Zeta potential | | particle size | |
|  | Prodn. | 24 h. | Prod. | 24 h. |
| Ciclosporin/POPG 50:3 (= 16.6:1) | | | | |
| Poloxamer 188 0.01% | −22.7 mV | −50.4 mV | 108.9 nm | 144.2 nm |
| Poloxamer 188 0.05% | −13.5 mV | −32.2 mV | 108.7 nm | 146.2 nm |
| Poloxamer 188 0.1% | −11.4 mV | −23.4 mV | 118.3 nm | 151.3 nm |
| Poloxamer 188 0.5% | −5.8 mV | −11.8 mV | 110.7 nm | 148.0 nm |
| Ciclosporin/PL 80 50:5 (= 10:1) | | | | |
| Poloxamer 188 0.01% | −17.7 mV | −19.0 mV | 139.9 nm | 143.1 nm |
| Poloxamer 188 0.05% | −10.3 mV | −11.0 mV | 132.4 nm | 145.8 nm |
| Poloxamer 188 0.1% | −7.8 mV | −8.5 mV | 127.1 nm | 144.1 nm |
| Poloxamer 188 0.5% | −2.3 mV | −2.1 mV | 165.6 nm | 170.4 nm |

As already mentioned, the addition of the poloxamer improves the re-dispersibility of spray-dried electrostatically stabilized colloidal particles. Comparison with particles not having the poloxamer shows that the poloxamer-containing particles are formed which are somewhat larger, however in solution can be applied intravenously with sufficient safety due to their small diameter.

Examples of pharmaceutical compositions in tablet form.

EXAMPLE 4

|  | mg | % |
|---|---|---|
| Cyclosporin A | 50 | 3.5 |
| Palmitoyl-oleyl-phosphatidyl-glycerol (POPG)(Stabilizer) | 1.7 | 0.1 |
| Lactose (carrier) | 1281.0 | 89.5 |
| Polysorbate 80 (poly-(20)-oxyethylated sorbitan monooleate, surfactant) | 17.0 | 1.2 |
| Sodium carboxymethyl cellulose (cross-linked, disintegrant) | 67.6 | 4.7 |
| Magnesium stearate (lubricating agent) | 6.8 | 0.5 |
| Aerosil (SiO$_2$) | 6.8 | 0.5 |
|  | 1430.9 | 100.0 |

EXAMPLE 5

| Cyclosporin G | 50 | 2.9 |
|---|---|---|
| POPG | 3.0 | 0.2 |
| Lactose | 1557.0 | 90.5 |

-continued

| | | |
|---|---|---|
| Polysorbate 80 | 21.0 | 1.2 |
| Na-carboxymethyl cellulose (cross-linked) | 81.7 | 4.7 |
| Magnesium stearate | 8.3 | 0.5 |
| | 1721.0 | 100.0 |

The cyclosporin particles, stabilized with POPG were prepared according to Example 1.

In the aqueous starting solution the poloxamer was replaced by polysorbate 80 (0.1%). The lactose concentration was 7.5%.

In the organic starting solution the cyclosporin and the POPG were present in a weight ratio of 10:1. The solvent was an aqueous solution of ethanol (60% of volume).

For the preparation of the colloidal particles the aqueous and the organic solution were admixed at the rates according to Example 1.

The spray-dried product was mixed with the desintegrant and concentrated in a compactor for dry powder. The granulate prepared was mixed with the lubricating agent and optionally with Aerosil and compressed to tablets (oblong 22.8×9.0 mm).

Dog Study

Six beagle dogs weighing around 12 kg were used. Twenty hours before the drug administration the food was withdrawn, but the animals were allowed free access to water until the beginning of the experiment.

The dosage form of Example 5 was orally administered to the animals, early in the morning (approx. 8.00 am), and followed by 20 ml NaCl 0.9% solution. Three hours after the administration, the animals were again allowed free access to water and food.

Blood samples of 2 ml (or 5 ml for the blank sample) were taken from the vena cephalica (forearm) and collected into 5 ml plastic tubes containing EDTA at −15 min, 30 min, 1, 1.5, 2, 3, 4, 6, 8 and 24 hours after the oral administration of the drug.

The whole blood samples of the animal studies were analysed with the SANDIMMUN radioimmunoassay kit from Incstar company. Still water, Minn. 55082, 1951 Northwestern Avenue, USA, using the non-specific monoclonal antibody (which also detects the drug metabolites).

Figure 4:
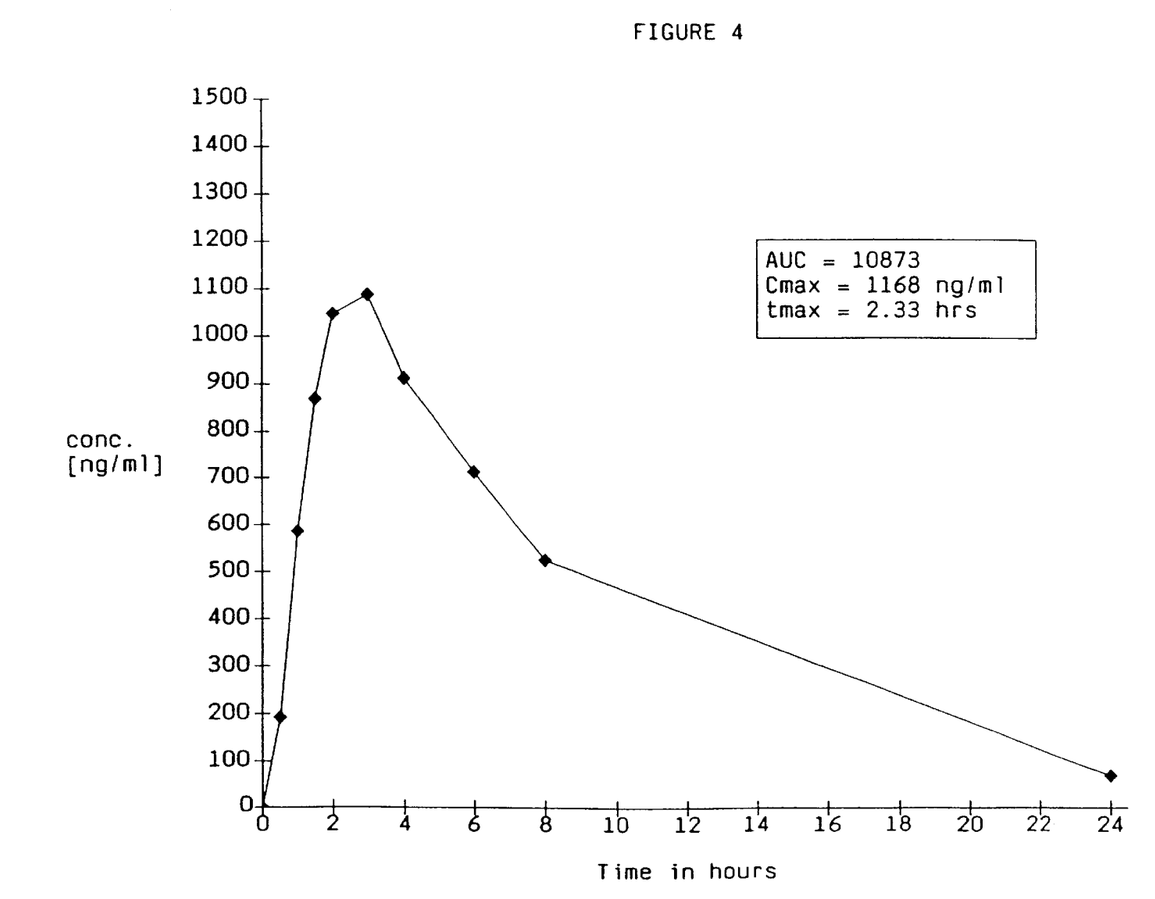
FIG. 4 represents the results of a bioavailability determination for the particles of the invention.

The test results were plotted in FIG. 4, showing an area under the curve from 0 to 24 hours ($AUC_o^{24}$) (=bioavailability) of 10873.

The invention thus especially provides a pharmaceutical composition comprising particles of Cyclosporin G, having on the surface thereof a colloid stabilizer and having an active substance: stabilizer weight ratio of 1:1 to 400:1, an average particle diameter, measured in liquid medium, of 1 nanometer to 10 micrometers and a bioavailability (=$AUC_o^{24}$), when the concentration is measured in ng/ml, of up to 11500, when orally administered in an amount of 50 mg of active substance to beagle dogs of 12 kg of body weight.

EXAMPLE 6

Effervescent Tablet

| | Amount | |
|---|---|---|
| | mg | % |
| Cyclosporin G | 50.0 | 1.3 |
| POPG | 3.0 | 0.08 |
| Lactose | 1557.0 | 39.7 |
| Polysorbate 80 | 21.0 | 0.52 |
| NaHCO$_3$ | 830.0 | 21.2 |
| Citric acid | 970.0 | 24.7 |
| Sucrose (for taste) | 325.0 | 8.3 |
| Polyethylene glycol 4000 (lubricant) | 115.0 | 2.9 |
| Orange aroma (for taste) | 20.0 | 0.5 |
| Aspartame (see Merck Index, 11th Edition, Monograph 861; sweetener) | 30.0 | 0.8 |
| | 3921.0 | 100.0 |

Shape/Size: Round/25 mm
Dissolution Rate
Medium: Water
Method: USP Paddle
UPM: 50

| Time (min) | % Released |
|---|---|
| 0 | 0 |
| 5 | 85.1 |
| 10 | 93.3 |
| 15 | 97.8 |
| 30 | 96.9 |
| 45 | 97.4 |

EXAMPLE 7

TABLET

| | Amount | |
|---|---|---|
| | mg | % |
| FK 506 | 10.0 | 2.3 |
| POPG | 0.7 | 0.2 |
| Lactose | 325.0 | 75.6 |
| Polysorbate 80 | 4.3 | 1.0 |
| Na-carboxymethyl cellulose (cross-linked) | 81.7 | 19.0 |
| Magnesium stearate | 8.3 | 1.9 |
| | 430.0 | 100.0 |

Shape/Size: Round/9.0 mm

What is claimed is:

1. Particles of a substantially water insoluble biologically active peptide having on the surface thereof a negatively or positively charged glyceryl ester which is a charged phospholipid obtained by extraction from natural lecithin or partially or completely by synthesis, the particles having a peptide charged ester weight ratio of from 30:1 to 50:1.

2. Particles of claim 1 wherein the peptide is a cyclopeptide.

3. Particles of claim 2 wherein the peptide is a cyclosporin.

4. Particles of claim 3 wherein the peptide is a cyclosporin having at water solubility of at most 40 μmL.

5. Particles of claim 3 wherein the peptide is cyclosporin A.

6. Particles of claim 3 wherein the peptide is cyclosporin G.

7. Particles of claim 3 wherein the peptide is [3'-desoxy-3'-oxo-MeBmt]$^1$-[Val]$^2$-clclosporin.

8. Particles of claim 3 wherein the peptide is [0–2-hydroxyethyl-D-Ser]$^8$-Ciclosporin.

9. Particles of claim 1 wherein the peptide is FK 506 or an analog thereof.

10. Particles of any preceding claim, which when placed in an aqueous 0.01 molar KCl solution have a zeta potential of −2.1 to −47.9 mV.

11. Particles of any one of claims 1 to 9 wherein the ester is phosphatidyl-glycerol, phosphatidyl-inosite; phosphatidyl-serine, or phosphatidic acid, or a salt thereof.

12. Particles of claim 10 wherein the ester is phosphatidyl-glycerol, phosphatidyl-inosite, phosphatidyl-serine, or phosphatidic acid, or a salt thereof.

13. Particles of any one of claims 1 to 9 which when dispersed in a liquid medium have an average particle diameter of from 80 nm to 10 micrometers.

14. Particles of claim 10 which when dispersed in a liquid medium have an average particle diameter of from 80 nm to 10 micrometers.

15. Particles of claim 13 having diameters of at most 0.3 micrometer.

16. Particles of claim 14 having diameters of at most 0.3 micrometer.

17. Particles of any one of claims 1 to 9 free from polymer or cross-linked wail, nucleus or matrix material.

18. Particles of claim 10 free from polymer or cross-linked wall, nucleus or matrix material.

19. A method of manufacturing a composition for therapeutic treatment, which comprises incorporating therein a particle of any one of claims 1 to 9.

20. A method of manufacturing a composition for therapeutic treatment, which comprises incorporating therein a particle of claim 10.

21. A pharmaceutical composition comprising particles of claim 1.

22. A pharmaceutical composition comprising particles of claim 10.

23. A pharmaceutical composition comprising particles of a biologically active peptide which is very poorly soluble in water and which are free from polymeric or cross linked nucleus, wall or matrix material, but loaded with a negatively or positively charged glyceryl ester as an electrostatic stabilizer which imparts to the particles a zeta potential of −2.1 to −47.9 mV when in an aqueous 0.01 molar KCl solution, the particles having a peptide: charged ester weight ratio of 30:1 to 50:1 and having diameters of 80 nm to 10 micrometers when measured in a liquid medium.

24. A pharmaceutical composition comprising colloidal particles of a pharmacologically active peptide which is very poorly soluble in water, with a negatively or positively charged glyceryl ester as an electrostatic phospholipid stabilizer which imparts to the particles a zeta potential of −2.1 to −47.9 mV in an aqueous, 0.01 molar KCl solution, and having a peptide:charged ester weight ratio of 30:1 to 50:1 and particle diameters, when measured in liquid medium, of 80 nm to 10 micrometers.

25. A composition of claim 23 or 24, comprising 0.01 μg/mL to 20 mg/mL of a cyclosporin dispersed in a liquid medium.

26. A composition of claim 23 or 24, comprising a carrier suitable for spray drying.

27. A composition of claim 23 or 24, comprising a sugar or sugar alcohol.

28. A composition of claim 23 or 24, comprising a surfactant.

29. A composition of claim 28, wherein the surfactant is a poloxamer.

30. A composition of claim 23 or 24 in powder form.

31. A composition of claim 29 in the form of suspensions, tablets, capsules, drink solutions, powders, salves, creams, gels, or suppositories.

32. A composition of claim 30 the form of suspensions, tablets, capsules, drink solutions, powders, salves, creams, gels, or suppositories.

33. A method for pulmonary administration to a subject in need thereof, which comprises administering to the lungs of said subject a therapeutically effective amount of a composition of any one of claims 21, 23, or 24 in powder form.

34. A pharmaceutical composition of claim 23 or 24 as a pulmonary inhalation solution in water.

35. An aqueous solution of a pharmaceutical composition of claim 23 or 24.

36. A method for oral administration to a subject in need thereof, which comprises administering to the mouth of said subject a therapeutically effective amount of a composition of any one of claims 21, 23, or 24.

37. A process for the production of the particles of any one of claims 1–9, comprising mixing a) an organic solution containing 1 to 100 mg/mL biologically active peptide and a negatively or positively charged glyceryl ester as an electrostatic stabilizer and b) an aqueous medium under conditions such that in the corresponding mixture the weight ratio of peptide to charged ester is from 30:1 to 50:1.

38. A process for the production of the particles of claim 10, comprising mixing a) an organic solution containing 1 to 100 mg/mL biologically active peptide and a negatively or positively charged glyceryl ester as an electrostatic stabilizer and b) an aqueous medium under conditions such that in the corresponding mixture the weight ratio of peptide to charged ester is from 30:1 to 50:1.

39. A process of claim 37, which comprises continuous mixing of separate currents of liquids a) and b).

40. A process of claim 38, which comprises continuous mixing of separate currents of liquids a) and b).

41. A process of claim 37, which comprises continuous mixing in a static mixer.

42. A process of claim 38, which comprises continuous mixing in a static mixer.

43. A process of claim 37, further comprising isolation of the resultant colloidal particles.

44. A process of claim 38, further comprising isolation of the resultant colloidal particles.

45. Particles produced by a process of claim 37, further comprising a carrier.

46. Particles produced by a process of claim 38, further comprising a carrier.

* * * * *